Oct. 22, 1946. H. C. SWIM Plant Pat. 713
ROSE PLANT
Filed Dec. 27, 1945
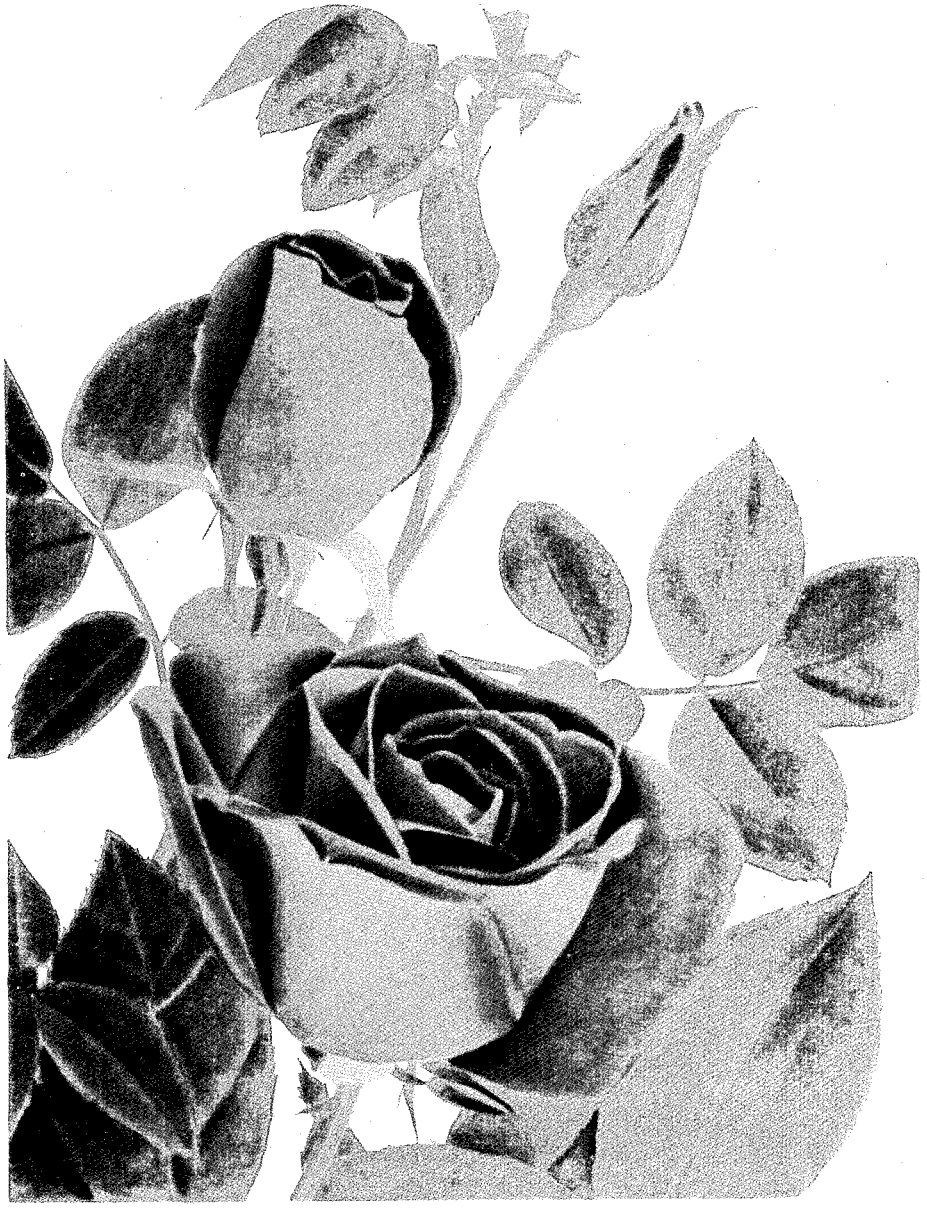
Inventor
H. C. Swim
By Robbins & Robbins
His attorneys Patented Oct. 22, 1946

Plant Pat. 713

UNITED STATES PATENT OFFICE

713

ROSE PLANT

Herbert C. Swim, Ontario, Calif., assignor to Armstrong Nurseries, Inc., Ontario, Calif., a corporation of California Application December 27, 1945, Serial No. 637,397

1 Claim. (Cl. 47—61)

The present invention relates to a new and distinct variety of rose plant, resulting from a cross of the known varieties "Charlotte Armstrong" (Pl. Pat. #455) and "Night," both of which produce flowers in the red range of colors.

This new variety, as far as color characteristic goes, more nearly approaches that of the variety "Mirandy" (Pl. Pat. #632), but it differs importantly therefrom in that its bud is much more slender and its blooms are composed of about half as many petals—therefore having a much different appeal than "Mirandy." These differences, more particularly pointed out hereinafter, have a decided practical or commercial value. That is to say, because of its slender bud, the new rose opens up much better in cool atmospheric conditions, than "Mirandy," while on the other hand, the latter is able to better withstand extreme heat, so that each variety has its own adaptability to different locations or climates.

Another advantageous difference is found in the fact that in the present rose, the foliage is more abundant, and while more susceptible to mildew, it is more resistant to Orange Rose rust. Furthermore, its fragrance is much more mild and of a spicy character, in comparison with the very heavy, sweet fragrance of "Mirandy."

Comparing this new variety with its parents, it may be noted that the wood and stems thereof resemble more nearly those of its seed parent, but it does not resemble the latter in any other respect except to a slight extent in its open-flower form. It has a flower with more substance and better lasting quality than that of its pollen parent.

Because of a greater degree of rust resistance, as before mentioned, this new rose is better suited to coastal planting, under the influence of fog, than either "Night" or "Mirandy," but it is not as well suited as "Mirandy" to inland areas where the heat is more severe during the summer, although it is superior in such areas to the variety "Night."

This new rose is characterized by its habit of producing more than one flower to a stem during the spring and early summer blooming period and by the production of only one flower to a stem during the late summer and fall blooming seasons, although the plants produce approximately the same number of blooms in the fall as in the spring season. Its adaptability for garden decoration uses serves to break the known scarcity of satisfactory garden varieties in the very dark red color range.

The drawing depicts a specimen of this new variety, its foliage and blooms in the bud, half-open, and full-open stages.

Asexual reproduction shows that the characteristics hold true through succeeding propagations.

The following is a detailed description of the new variety, all references to color being in accordance with the R. F. Wilson's Horticultural Colour Chart, except where indicated to be in according with Ridgway's Color Standard and Nomenclature:

Type: Hardiness untested; bush; outdoor; seedling; for cut flowers and garden decoration.
Class: Hybrid tea.
Breeding: Seedling.
*Seed parent.*—"Charlotte Armstrong."
*Pollen parent.*—"Night."
Propagation: By budding, the only method tried so far.

*Flower*

Locality where grown: Ontario, California.
Flowers borne: Singly, sometimes two or more, to stem; in irregular cluster; on normally strong, medium to long stems.
Quantity of bloom: Abundant; outdoors.
Continuity: Continuous during growing season.
Fragrance: Moderate; spicy.
Bud:
*Peduncle.*—Long; medium weight; erect; almost smooth; few gland-tipped cilia and prickles. *Color*—near Rainette Green, Plate XXXI (Ridgway), on shady side, to Morocco Red, Plate I (Ridgway), on side exposed to sun.
*Before calyx breaks.—Size*—medium. *Form*—long; pointed; with foliaceous appendages, slight glandular bloom on the surface of the bud; with slender, much cut foliaceous parts extending beyond the tip of the bud equal to ¾ or more of its length.
*As calyx breaks.—Color*—Maroon, Plate 1030, page 185, to Maroon, Plate 1030/3, page 185. Inner surface—with fine, woolly tomentum. When the margin of a sepal is not covered by the margin of an adjacent sepal, it has woolly tomentum and stipitate glands on both margins; but if margin is covered with adjacent sepals, margin has only woolly tomentum.
*As first petal opens.—Size*—large. *Form*—long; pointed. *Color*—outside—Indian Lake, Plate 826, page 170, at tip; Ruby Red, plate 827, page 171, at base, with Maroon, Plate 1030, page 185, shadings; inside—

Ruby Red, Plate 827, page 171, to Indian Lake, Plate 826, page 170, with Maroon, Plate 1030, page 185, shadings.

*Opening.*—Opens up well.

Bloom:

*Size.*—When fully open, medium large; 3¼ inches to 4¾ inches.

*Petalage.*—Double but the stamens not hidden; from 20 to 28 petals, plus 3 to 5 petaloids, arranged regularly.

*Form.*—Very high centered at first; becoming open; petals remaining at first loosely cupped with tips rolled outward; becoming later, at maturity, flat-cupped with tips reflexed.

Petals: Medium thick; moderately leathery; with inside velvety and outside shiny.

*Shape.* — Outside — broadly obovate; scalloped with apex flat, with 2 to 3 notches. Intermediate—broadly obovate; scalloped with apex flat, with 1 to 2 notches. Inside—obovate oblong; with apex flat, with 1 notch.

*Color.*—Colors may be modified by being shaded with other colors.

This description of a newly opened flower was made from a rose grown outdoors in the month of October, 1945, at Ontario, California, in cool, cloudy weather:

*Color.*—*Outside petal*—outside surface; Indian Lake, Plate 826, page 170; inside surface: Chrysanthemum Crimson, Plate 824–3, page 169, with Indian Lake, Plate 826, page 170, shading. *Intermediate petal*—outside surface: Indian Lake, Plate 826/1, page 170; inside surface: Chrysanthemum Crimson, Plate 824/1, page 169, with Indian Lake, Plate 826, page 170, shading. *Inner petal*—outside surface: Indian Lake, Plate 826/1, page 170; inside surface: Chrysanthemum Crimson, Plate 824/1, page 169, with Indian Lake, Plate 826, page 170, shading.

This description was made from a rose that was open for three days outdoors in the month of October, 1945, at Ontario, California, in cool, cloudy weather, approximately 75° F. mid-day:

*Outside petal.* — Outside surface — Indian Lake, Plate 826, page 170. Inside surface—Ruby Red, Plate 827, page 171, to Chrysanthemum Crimson, Plate 824/2, page 169, at base, with apex Maroon, Plate 1030, page 185.

*Inside petal.*—Outside surface—Chrysanthemum Crimson, Plate 824/1, page 169. Inside surface—Indian Lake, Plate 826, page 170, to Chrysanthemum Crimson, Plate 824/2, page 169, at base, with Maroon, Plate 1030, page 185, at apex.

*General color effect.*—Newly opened flower—Chrysanthemum Crimson, Plate 824/1, page 169, with Indian Lake, Plate 826, page 170, shading. Three days open—near Indian Lake, Plate 826, page 170, with Maroon, Plate 1030, page 185, shading, bordered at apex by Maroon, Plate 1030, page 185.

*Behavior.*—Drop off cleanly except for petaloids; fading to near Aster Purple, plate XII (Ridgway), with shading of Rosalane Purple, Plate XXVI (Ridgway) near base; affected by hot weather by fading slightly in hot weather to a lighter color.

*Flower longevity.*—On bush in garden—three days in October. Cut flowers, grown outdoors, kept at living room temperatures—three to four days in October.

*Reproductive organs*

Stamens: Medium number; arranged regularly about pistils, mixed with petaloids.

Filaments: Medium length; ¼ inch to ½ inch long. *Color*—Jasper Red, Plate 018/1, page 107, changing to Orange Buff, Plate 507, page 133, at base. Most with anthers.

Anthers: Medium size; all open at once approximately. *Color*—Spinel Pink, Plate 0625/2, page 184, at center, and Yellow Ochre, Plate 07/2, page 101, at margin, from fully open flower.

Pollen: Moderately abundant; Yellow Ochre, Plate 07/1, page 101.

Pistils: Medium number; approximately forty.

Styles: Moderately uneven; medium length, average about 10/32″ in length; medium heavy; loosely bunched. *Color*—near Currant Red, Plate 821, page 167, near stigma, becoming somewhat lighter at base.

Stigma: Grayish-white with a pink shade from style—more or less translucent.

Ovaries: Most enclosed in, few protruding from, calyx.

Hips: Short; globular; matured hips near Aniline Yellow, Plate IV (Ridgway), blotched with near Brazil Red, Plate I (Ridgway) on side exposed to sun. These two colors both are blotched with a corky callus of a color near Sayal Brown, Plate XXIX (Ridgway). Moderately smooth; walls ⅛″ thick; fleshy.

Sepals: Permanent; moderately long; recurved but curved upwards at tip. *Color*—inside—sepals from fully-open flower—inside color, Chromium Green, Plate XXXII (Ridgway) at tip, having an Acajou Red, Plate XIII (Ridgway) center near base. Sepals from matured hips (sepals not yet dried)—color inside, near Lime Green, Plate XXXI (Ridgway) to near Clay Color, Plate XXIX (Ridgway). Outside—Sepals from fully-open flower—outside color, near Turtle Green, Plate XXXII (Ridgway) at tip, becoming Chromium Green, Plate XXXII (Ridgway) near base, with slight Acajou Red, Plate XIII (Ridgway) in center near base. Sepals from matured hips (sepals not yet dried) near Citron Green, Plate XXXI (Ridgway) to near Clay Color, Plate XXIX (Ridgway) near base.

Seeds: Ten to fifteen; medium size.

*Plant*

Foliage:

*Leaves.*—Compound of five to seven leaflets; moderately abundant; medium to large; moderately heavy; somewhat leathery.

*Leaflets.*—Shape—oblong; lanceolate with apex acute; base round; margin doubly serrate.

*Color.* — *Mature* — upper surface — Cedar Green, Plate VI (Ridgway); under surface—Light Elm Green, Plate XVII (Ridgway). *Young*—upper surface—near Morocco Red, Plate I (Ridgway), gradually becoming various shades of green as leaves mature, until color is Cedar Green, Plate VI (Ridgway); under surface—near Vandyke Red, Plate XIII (Ridgway), gradually becoming various shades of green as leaves mature, until color is Light Elm Green, Plate XVII (Ridgway).

*Rachis.*—Medium heavy; upper side grooved with few stipitate glands on edges; under side moderately prickly and with stipitate glands.

*Stipules.*—Medium long; medium wide; with medium long points, turning out at an angle of more than 45°, recurved toward the stem.

*Disease.*—Mildly subject to mildew.

Growth:

*Habit.*—Bushy; upright; much branched.

*Growth.*—Vigorous.

*Canes.*—Medium heavy.

*Main stems.*—Light Cress Green, Plate XXXI (Ridgway), with near Clay Color, Plate XXIX (Ridgway), from stripes of callus formed by splitting of epidermal bark layer. *Large prickles*—several; medium length; hooked slightly downward; with medium long, narrow base. Color—near Snuff Brown, Plate XXIX (Ridgway). *Small prickles*—few. Color—Snuff Brown, Plate XXIX (Ridgway). *Hairs*—none.

*Branches.* — Asphodel Green, Plate XLI (Ridgway) on semi-hardwood branches. *Large prickles*—several; medium long; hooked slightly downward; with medium long, narrow base. Color—near Buff Pink, Plate XXVIII (Ridgway). *Small prickles*—several. Color—near Vandyke Brown, Plate XXVIII (Ridgway). *Hairs*—none, but branches have stipitate glands on semi-mature wood.

*New shoots.*—Deep Dull Yellow-Green (1), Plate XXXII (Ridgway). *Large prickles*—several; medium long; hooked slightly downward; with medium long, narrow base. Color—Chrysanthemum Crimson, Plate 824/3, page 169. *Small prickles*—several, Color—Chrysanthemum Crimson, Plate 824/3, page 169. *Hairs*—none. New shoots have stipitate glands.

I claim:

A new and distinct variety of Rose plant, characterized as to novelty by the color of its flowers; the slender form of its buds; the number of petals and petaloids; the lasting quality of the flowers; their mild fragrance; the resistance of its foliage to Orange Rose rust; and its habit of producing more than one bloom per stem in the early part of its blooming season and a single bloom to a stem during the late blooming period, substantially as shown and described.

HERBERT C. SWIM.